(12) United States Patent
Lin et al.

(10) Patent No.: US 8,513,014 B2
(45) Date of Patent: Aug. 20, 2013

(54) METHOD FOR FABRICATING FOAM SCAFFOLDS TO CULTURE CELLS

(75) Inventors: Keng-Hui Lin, Taipei (TW); Narayan Mishra, Saharanpur (IM); Yen-Liang Liu, Shalu Township (TW); Chen-Chie Wang, Sindian (TW)

(73) Assignee: Academia Sinica, Taipei (TW)

( * ) Notice: Subject to any disclaimer, the term of this patent is extended or adjusted under 35 U.S.C. 154(b) by 809 days.

(21) Appl. No.: 12/582,575

(22) Filed: Oct. 20, 2009

(65) Prior Publication Data

US 2011/0091972 A1    Apr. 21, 2011

(51) Int. Cl.
*C12N 5/00* (2006.01)
*C12N 5/07* (2010.01)
*C12M 1/00* (2006.01)

(52) U.S. Cl.
USPC ................ 435/395; 435/325; 435/283.1

(58) Field of Classification Search
None
See application file for complete search history.

(56) References Cited

U.S. PATENT DOCUMENTS

| | | | | |
|---|---|---|---|---|
| 6,511,650 | B1 * | 1/2003 | Eiselt et al. | 424/44 |
| 7,056,957 | B2 * | 6/2006 | Omidian et al. | 521/99 |
| 7,708,949 | B2 * | 5/2010 | Stone et al. | 422/502 |
| 2006/0002978 | A1 * | 1/2006 | Shea et al. | 424/426 |
| 2007/0286880 | A1 * | 12/2007 | Vasiliev et al. | 424/422 |

OTHER PUBLICATIONS

Arumuganathar, S. et al., "Aerodynamically Assisted Jets: A Paradigm for Directly Microbubblig and microfoaming Combinations of Advanced Materials," Advanced Materials, 20: 4419-4422 (2008).
Chung, K.-Y. et al., "Fabricating scaffolds by microfluidics," Biomicrofluidics, 3, 022403-1 to 024403-8 (Apr. 21, 2009).
Eiselt, P., "Porous carriers for biomedical applications based on alginate hydrogels," Biomaterials, 21: 1921-1927 (2000).
Lorenceau, E. et al., "A High Rate Flow-Focusing Foam Generator," Physics of Fluids, 18, 097103-1 to 097103-5, (2006).
Shah, R.K. et al., "Designer emulsions using microfluidics," Materials Today, 11(4): 18-27 (Apr. 2008).
Utada, A.S., "Dripping, Jetting, Drops, and Wetting: The Magic of Microfluidics," MRS Bulletin 32: 702-708 (Sep. 2007).
Utada et al., :"Monodisperse Double Emulsions Generated from a Microcapillary Device", Science, vol. 308, Apr. 22, 2005, pp. 537-541.

* cited by examiner

*Primary Examiner* — David M Naff
(74) *Attorney, Agent, or Firm* — Perkins Coie LLP

(57) ABSTRACT

Methods and apparatuses for using microfluidics to generate bubbles and using the generated bubbles to construct scaffolds and cell-holding structures for culturing biological samples or analytes. In one implementation, a scaffold for growing cells is provided to include a matrix of interconnected cavities formed from mixing a gas and a liquid containing a cross linkable material to produce a matrix of gas bubbles of substantially the same size and cross linking the cross linkable material to form a structure in which cells are grown. In another implementation, a scaffold apparatus for growing cells includes a ball of a cross linked material forming an exterior shell that encloses to form a hollow interior inside the ball and biological samples embedded in the external shell.

20 Claims, 13 Drawing Sheets

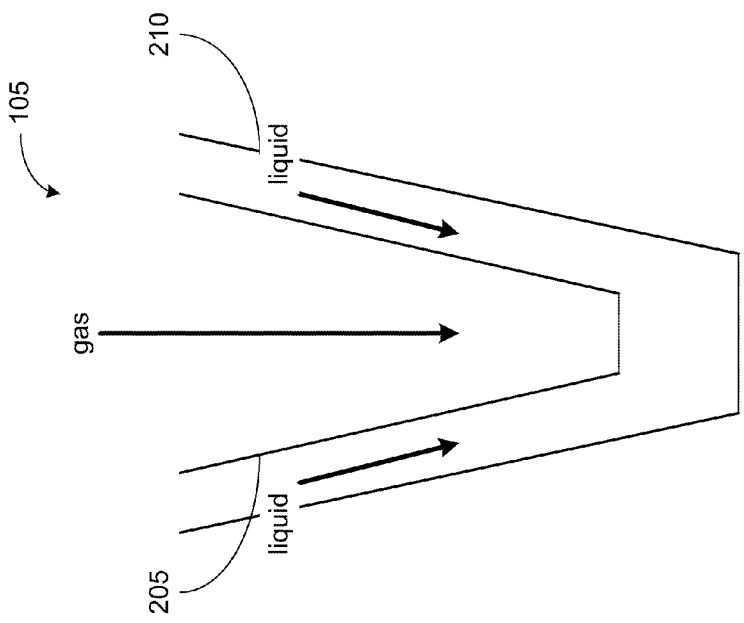
FIG. 2B
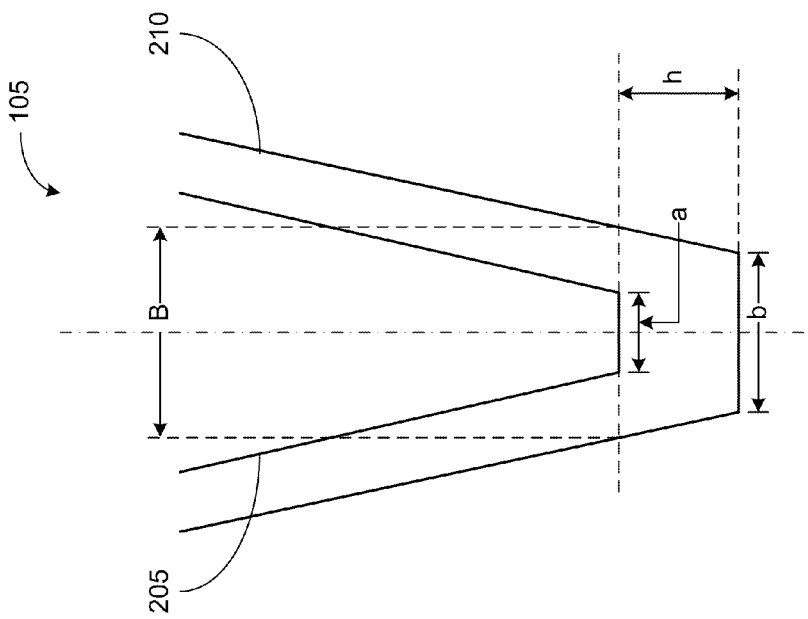
FIG. 2A
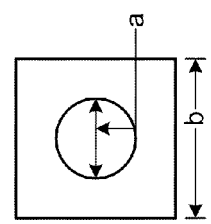

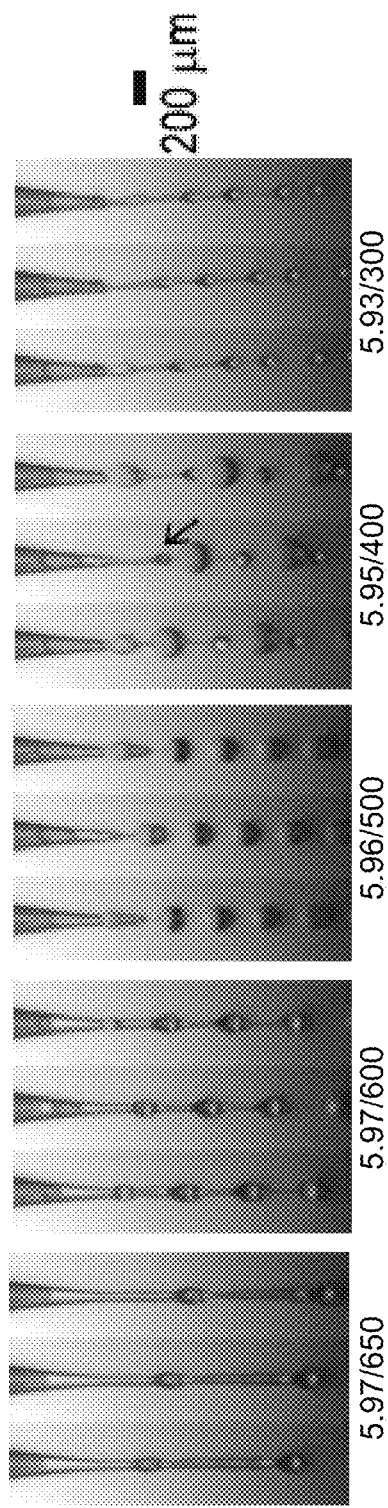

4.03/400

3.65/300

4.03/350

4.19/400

7.04/600

8.04/500

7.05/300

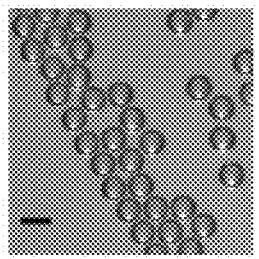 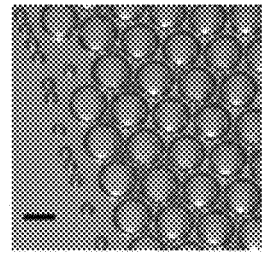 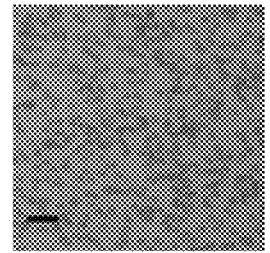
FIG. 9A    FIG. 9B    FIG. 9C
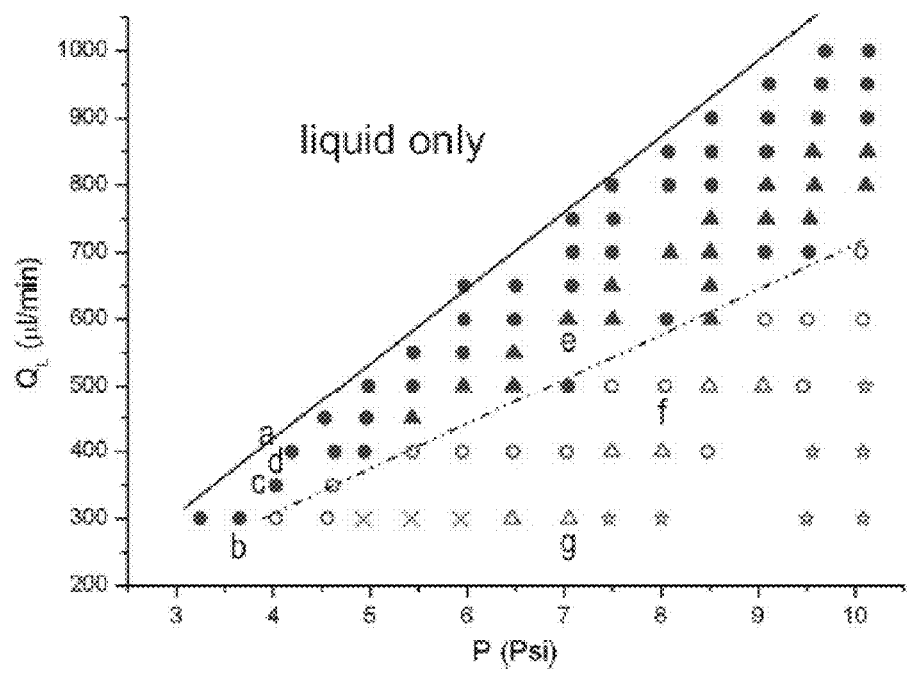
FIG. 10

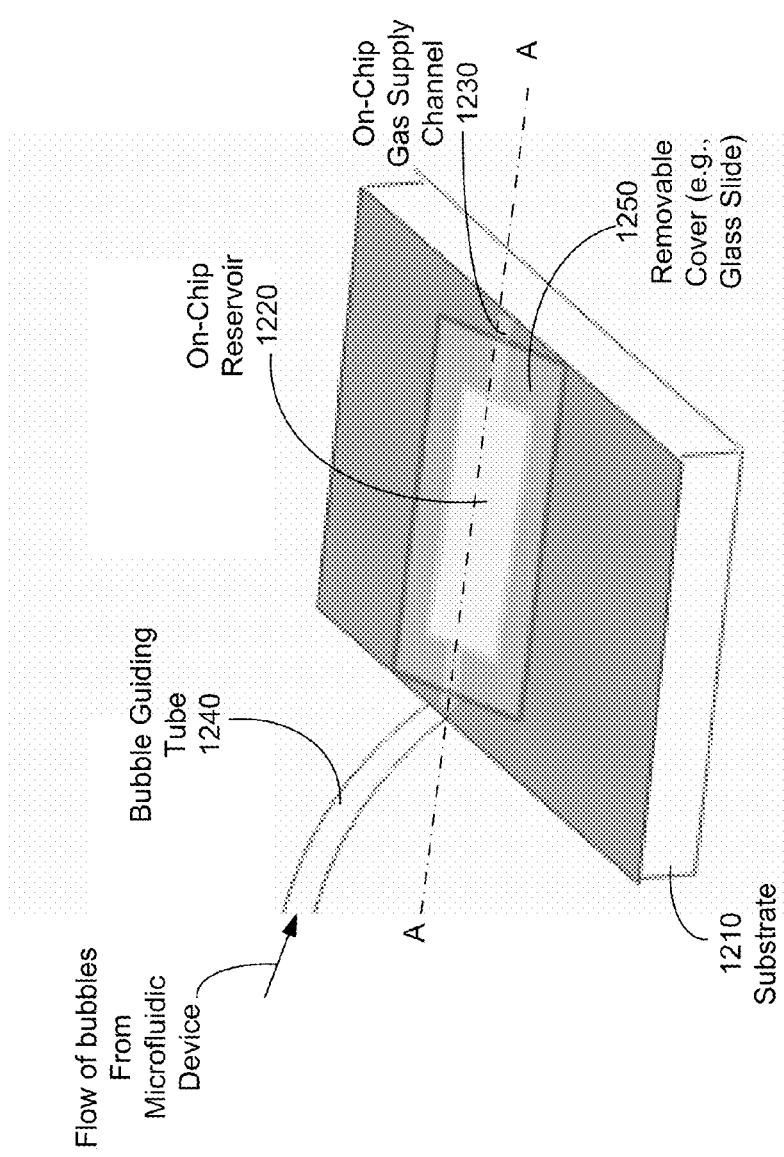
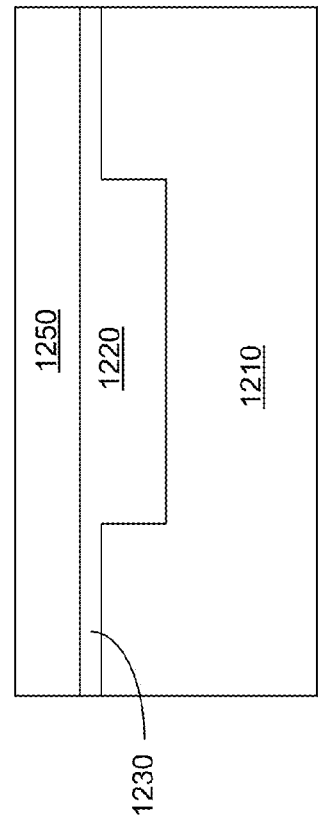
FIG. 12A
FIG. 12B

US 8,513,014 B2

METHOD FOR FABRICATING FOAM SCAFFOLDS TO CULTURE CELLS

TECHNICAL FIELD

This patent document relates to techniques, structures and apparatus for growing biological samples including cells for tissue engineering and other applications.

BACKGROUND

Growth of biological samples such as cells under controlled conditions is important in tissue engineering and various applications. Various cell-growth structures can be used to hold desired cell samples. Examples of some cell-growth structures used for growing cells include Petri dishes, tissue culture flasks, porous structures or matrixes as scaffolds.

SUMMARY

This document describes exemplary methods and apparatuses for using microfluidics to generate bubbles and using the generated bubbles to construct scaffolds and cell-holding structures for culturing biological samples or analytes.

In one implementation, for example, a scaffold apparatus for growing cells is provided to include a matrix of interconnected cavities formed from mixing a gas and a liquid containing a cross linkable material to produce a matrix of gas bubbles of substantially the same size and cross linking the cross linkable material to form a structure in which cells are grown.

In another implementation, a scaffold apparatus for growing cells includes a ball of a cross linked material forming an exterior shell that encloses to form a hollow interior inside the ball and biological samples embedded in the external shell.

In another implementation, a method is provided to include providing a liquid mixture of a cross-linkable liquid and biological samples; mixing a gas with the liquid mixture to generate monodispersed bubbles each formed by encapsulating the gas inside a ball of the liquid mixture; and causing the bubbles to be in contact with a solution of a cross-linking reagent to transform the encapsulating liquid mixture in the monodispersed bubbles into a foam via crosslinking of the cross-linkable liquid.

In another implementation, a method is provided for fabricating scaffolds to culture cells and includes mixing a gas with a liquid including a crosslinkable material in solution to generate gas bubbles having respective diameters in a micrometer range; collecting the generated gas bubbles in a volume to assemble the collected gas bubbles relative to one another to form a stack of gas bubbles in form of a liquid foam; causing the crosslinkable material on a gas bubble to cross-link to transform the liquid into a foam in which the gas bubbles form a matrix of cavities inside the foam; and treating the foam to form a scaffold which provides cavities for cell growth.

In yet another implementation, an apparatus for producing gas bubbles is provided to include an outer micropipette including an outer outlet having an outer outlet dimension and configured to allow a liquid to flow through, and an inner micropipette located inside the outer micropipette to separate the interior within the outer micropipette into a gas flow region inside the inner micropipette and a liquid flow region between the inner micropipette and the outer micropipette. The inner micropipette includes an inner outlet having an inner outlet dimension to allow a gas to flow through and to mix with the liquid before the liquid flows through the outer outlet to produce gas bubbles inside the liquid at the outer outlet. This apparatus includes a first fluid inlet coupled to inner micropipette to receive the gas to pass through the inner micropipette; and a second fluid inlet coupled to the outer micropipette to receive the liquid to pass through the region inside the outer micropipette and between the outer micropipette and the inner micropipette.

Particular implementations of the subject matter described in this document can be implemented to realize one or more of the following advantages. Using the microfluidic techniques described here, scaffolds of uniform pore sizes can be developed for tissue engineering and cell cultures. Such scaffolds, that have ordered and uniform spatial structures, can enable elucidating the effect of cell-to-cell and cell-to-matrix interactions due to structure. Further, the uniform spatial structure can facilitate the homogenous distribution of chemical stimuli that modify the scaffolds, such as, bioactive molecules including growth factors, drugs, adhesion peptides, and the like. Data shows that chondrocytes proliferate in the scaffolds. Micro-environments can be created to study the effect of pore size and porosity in tissue engineering. Further, systematic studies on the architectural influence of the differences in signaling, gene expression, and organization can be studied. Furthermore, the 3D structures created for the proliferation of cells can more accurately simulate the 3D extracellular matrix that supports the growth of tissue cells. Also, the techniques to create the micro-environment that includes the scaffolds can be simplified and made fast, and inexpensive. Various cell growth structures described in this document can be configured in compact forms for ease of use and transportation.

The details of one or more implementations are set forth in the accompanying drawings, the description and the claims.

BRIEF DESCRIPTION OF THE DRAWINGS

FIGS. 2A and 2B show an example of a microfluidic system for generating bubbles.

FIGS. 3A-3E shows morphology of liquid droplets containing bubbles.

FIGS. 9A-9C show images of collected bubbles.

FIG. 10 is a plot of liquid flow rate versus gas pressure.

FIGS. 12A and 12B show another example of an apparatus for collecting gas bubbles and for performing crosslinking.

Like reference numbers and designations in the various drawings indicate like elements.

DETAILED DESCRIPTION

Figures 1A, 1B:
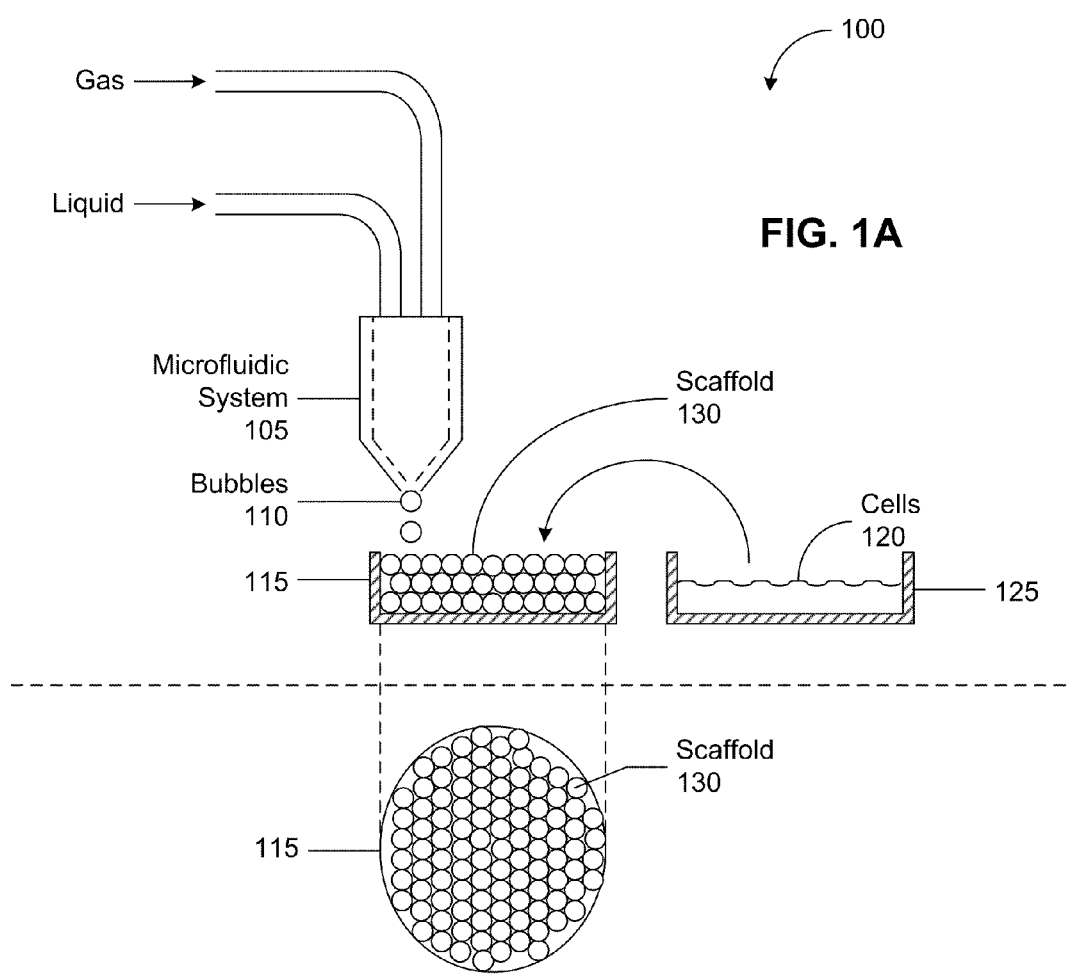
FIGS. 1A and 1B show an example of a system for fabricating scaffolds using microfluidics to culture biological cells.

Methods, apparatuses, and systems for using microfluidics to generate bubbles from cross-linkable liquids and to fabricate cell-growth structures and tissue engineering scaffolds are described. The generation of the bubbles can be controlled to produce bubbles of substantially uniform diameters and having a liquid shell formed of a cross-linkable liquid including a cross linkable polymer in which cross linking can occur in presence of a suitable cross linking reagent. The generated bubbles can be collected in form of various dispersed states, e.g., 2-dimensional (2D) or 3-dimensional (3D) matrices, and monodispersed bubbles. The collected bubbles are exposed to a solution having the suitable crosslinking reagent to cause the crosslinking of the polymer, turning the liquid shell into a shell of a foam. Cell samples can be embedded inside the foam or located in the space outside the foam.

Tissue cells in the body grow in a three-dimensional (3D) matrix known as an extracellular matrix. To grow a functional tissue or organ, cells need be cultured in a three-dimensional (3D) structure for various uses. Differences, for example, phenotypes, exist between cells grown in 2D versus 3D cultures. 3D porous matrices can be used to construct scaffolds that support cell growth on or within their structures, and, consequently, can be used to perform 3D cell culture studies. Examples of techniques for producing 3D scaffolds include freeze drying, phase separation, particle leaching, electrospraying, and electrospinning. 3D scaffolds produced by these techniques tend to have pores with a wide distribution in sizes and shapes for lacking of control over the sizes and shapes of the 3D porous matrices. The techniques described in this document allows production of bubbles of substantially uniform sizes and shapes and can be used for forming 3D porous matrices of spatially uniform pores. In some implementations, the techniques described in this document can be used for forming 2D matrices with improved uniformity in structure than 2D matrices formed by using other devices, such as in vitro cell cultures using Petri dishes and tissue culture flasks. In other implementations, the techniques described in this document can be used to form monodispersed hollow balls with cell samples embedded in the ball shells.

In fabricating scaffolds that have uniform pore sizes, gas and liquid can be pumped through two concentrically positioned micro-pipettes to generate gas bubbles inside the liquid and the generated bubbles are used to fabricate scaffolds. A solidified foam generated by collecting and treating the bubbles can be used to form a tissue engineering scaffold. The choice of gas and liquid, and flow rates is used to produce and control desired patterns of bubbles of different sizes, that are encapsulated in liquid droplets. Further, in some implementations, monodisperse bubbles that are of the same size are created and self-assemble into crystalline structures that form liquid crystalline foams. The liquid crystalline foams can be processed into open-cell solid foams for use as a scaffold to culture biological analytes, for example, chondrocytes. A system for culturing cells by using such a scaffold is described with respect to FIGS. 1A and 1B.

FIGS. 1A and 1B show an example of a system 100 for fabricating a scaffold 130 using microfluidics to culture biological cells. The system 100 includes a microfluidic system 105 having an inner micropipette for carrying and conducting a gas and an outer micropipette for carrying and conducting a liquid that contains at least a cross-linkable material to be mixed with the gas, as described in detail with reference to FIGS. 2A and 2B. A gas inlet 106 is provided to supply the gas to the inner micropipette and a liquid inlet 107 is provided to supply the liquid to the outer micropipette. The microfluidic system 105 produces multiple gas bubbles 110 at an outlet 108. Each bubble 110 includes the liquid encapsulating the gas. The dimensions of the microfluidic system 105, particularly at the outlet 108, and those of the bubbles 110 produced by the microfluidic system 105 can be in the micrometer range. Specific exemplary ranges of dimensions are described later. The bubbles 110 can be accumulated in a container or holder 115 such as a vessel 115. In some implementations, the vessel 115 is a culture plate including one or more wells. In such implementations, the bubbles 110 can be collected in one or more wells of the culture plate 115. In other implementations, the bubbles 110 can be collected in a Petri dish or other containers.

As shown in FIGS. 1A and 1B, in some implementations, the microfluidic system 105 can be controlled to form monodisperse bubbles 110, each of which has substantially the same diameter. The monodisperse bubbles 110 self-assemble to form crystalline structures. In some implementations, the self-assembled monodisperse bubbles 110 can be processed to form scaffolds 130. As described later, cells 120, extracted from tissues and collected in a vessel 125, can be introduced into the scaffold 130. In this manner, the scaffold 130 provides a 3D environment in which the cells 120 can be cultured.

The structure and operation of the microfluidic system 105 that produces bubbles 110 to form the scaffold 130 are described with respect to FIGS. 2A and 2B.

In the example in FIGS. 2A and 2B, the microfluidic system 105 generates bubbles 110 suitable for forming the scaffold 130. The microfluidic system 105 includes two micropipettes 205 and 210. A micropipette can include a tubular device having an inlet and an outlet and a region between the inlet and the outlet configured to carry and conduct a fluid to flow in between. The dimensions of the outlets of micropipettes can be in the micrometer range for various applications. For example, if the micropipette has a circular cross-section, then the diameter of the inner wall at the outlet of a micropipette lies in a range between and including 10 μm and 1000 μm. In another example, if the micropipette has a square cross-section, then the length of a side of the inner wall at the outlet of the micropipette lies in the 10 μm-1000 μm range. For various uses, the dimensions of the inlets of the micropipettes may also be in the micrometer range, and can, but need not, be substantially equal to, the dimensions of the outlets.

In some implementations, the tubular inner micropipette 205 and the tubular outer micropipette 210 can each have respective inner and outer dimensions, for example, respective inner and outer thicknesses. The outer dimension of the inner micropipette 205 is less than the inner dimension of the outer micropipette 210. When the inner micropipette 205 is positioned within the outer micropipette 210, a region can be formed between the outer dimensions of the inner micropipette 205 and the inner dimensions of the outer micropipette 210. The inner micropipette 205 located inside the outer micropipette 210 separates the interior within the outer micropipette 210 into a gas flow region inside the inner micropipette 205 and a liquid flow region between the inner micropipette 205 and the outer micropipette 210. The inner micropipette 205 includes an inner outlet having an inner outlet dimension to allow the gas to flow through and to mix with the liquid before the liquid flows through the outer outlet to produce gas bubbles inside the liquid at the outer outlet. Referring to FIGS. 1A and 1B, the microfluidic system 105 includes the gas inlet 106 coupled to the inner micropipette 205 to receive the gas to pass through the inner micropipette 205, and the liquid inlet 107 coupled to the outer micropipette 210 to receive the liquid to pass through the region inside the outer micropipette 210 and between the outer micropipette 210 and the inner micropipette 205. In such an arrangement, when the liquid is flowed into the outer micropipette 210, the liquid flows through the outer micropipette 210, and through the region between the inner micropipette 205 and the outer micropipette 210.

The microfluidic system 105 can include multiple micropipettes and can be configured to place one micropipette within another. For example, a microfluidic system can include three micropipettes, each positioned within another. The micropipettes can be arranged such that the inlet of each micropipette can receive a respective fluid, for example, liquid or gas. The outlets of the micropipettes can be arranged such that the fluid that passes through the outlet of a first micropipette that is positioned within a second micropipette also passes through the outlet of the second micropipette. In the example microfluidic system including three micropipettes, a liquid or a gas can be pumped through any of the three micropipettes.

In some implementations, the two micropipettes 205 and 210 are concentrically positioned, as illustrated in FIG. 2A. In such implementations, the outlet of the inner micropipette 205 is parallel to the outlet of the outer micropipette 210. Alternatively, the axis of one micropipette can be off-set from that of the other. Alternatively, or in addition, the outlets of the two micropipettes can be off-set to be non-parallel to each other. In some implementations, the cross-section of the inner micropipette 205 can be a circle, and that of the outer micropipette 210 can be a square. In such implementations, the diameter, "a," of the circle representing the cross-section of the inner micropipette 205 can be substantially the same as, yet less than, the inner dimension, "b," of the square representing the cross-section of the outer micropipette 210. In some implementations, the inner micropipette 205 can be nestled within the outer micropipette 210 to have a configuration as shown in FIG. 2A. In such implementations, the diameter, "a," can be between 25 μm and 30 μm, and the dimension, "b," can be between 60 μm and 75 μm.

In some implementations, the inner micropipette 205 and the outer micropipette 210 can each have a frusto-conical shape. In alternative implementations, the sides of each micropipette can be substantially parallel to one another, and can taper at the end such that only the ends of the micropipettes are frusto-conical. In some implementations, after the inner micropipette 205 is positioned inside the outer micropipette 210, the tip-to-tip distance between the two micropipettes, "h," can be between 350 μm and 450 μm. In some scenarios, an outlet of the inner micropipette 205 can be positioned parallel to the outlet of the outer micropipette 210. In such scenarios, a region including a plane intersecting the sides of the outer micropipette 210 and on which the outlet of the inner micropipette 205 lies, and the outlet of the outer micropipette 210 can form a frusto-conical shape having a base. The diameter of the base, "B," can be between 350 μm and 450 μm. Note that these dimensions are representative dimensions only. Micropipettes having cross-sectional dimensions outside the ranges specified above can be positioned at distances also outside the ranges specified above.

The micropipettes 205 and 210 can be fabricated by pulling using a micropipette puller, for example, a P-97 micropipette puller manufactured by Sutter Instrument (California, USA). As shown in FIG. 2B, gas and liquid can be flowed through the inner micropipette 205 and the outer micropipette 210, respectively. For example, nitrogen gas can be pumped through the inner micropipette 205 and a fluid can be flowed through the outer micropipette 210. In some implementations, the fluid can be a filtered aqueous solution including 1% alginate, made using alginic acid sodium salt from brown algae (A2158), available at Sigma Aldrich (Missouri, USA). In addition to the 1% alginate, the fluid can include a cell encapsulating material, for example, a block copolymer such as Pluronic® F127 surfactant provided by BASF Corporation (California, USA). In some implementations, the fluid can include 1% Pluronic® F127 surfactant because cells can proliferate and maintain high viability at this concentration of Pluronic® F127. The fluid can be injected through the outer micropipette 210 at a controlled flow rate using a syringe pump, for example, one provided by Harvard Apparatus (Massachusetts, USA). The pressure can be measured using a digital pressure indicator, for example, a PM digital pressure indicator provided by Heise (Connecticut, USA). As described later, the diameters of the bubbles formed by injecting fluids through the inner micropipette 205 and the outer micropipette 210 were distributed in the micrometer ranges, and more particularly in ranges between and including 40 μm and 180 μm.

In the example in FIGS. 1A and 1B, the microfluidic system 105 is shown as a single unit that produces a single stream of bubbles 110. In other implementations, two or more microfluidic systems 105 can be used to form an array that produces two or more streams of bubbles 110 into the vessel 115.

FIGS. 3A-3E show examples of morphology of liquid droplets containing bubbles generated by an array of three microfluidic systems under various operating conditions. The bubble formation process was imaged by an ultrahigh speed video camera (Phantom v 4.2 provided by Vision Research, USA). The exposure time of the video cameras was 10 μs and the images were captured in a reduced size (64×256) at a frame rate of 20,000 frames/second. The bubbles were created by pumping gas at a nearly constant pressure between 5.93 psi and 5.97 psi and decreasing the flow rate of the fluid from FIG. 3A through FIG. 3E. Each of FIGS. 3A-3E denotes the ratio of the gas pressure and the liquid flow rate in term of pressure (psi) and flow rate in (/min). Specifically, FIG. 3A shows a jet generated by each of the three microfluidic systems, FIG. 3B shows a thinning jet generated by each of the three microfluidic systems at a reduced flow rate, FIG. 3C shows monodisperse droplets, i.e., bubbles 110, FIG. 3D shows bidisperse droplets, and FIG. 3E shows only small droplets. Further, FIG. 3D also shows a burst bubble.

Bubble formation occurs at the cavity between the inner orifice and the outer orifice of the inner micropipette 205 and the outer micropipette 210, respectively. The gas stream expands at the exit of the inner orifice, constricting the passage of the fluid flow, and eventually breaking up into bubbles. The liquid flow containing bubbles inside changes from jetting to dripping when the liquid flow rate is decreased, as shown in FIGS. 3A-3E. The liquid bridge between the bubbles becomes thinner and shorter and eventually disappears. The very thin filament-like bridge is the characteristic of viscoelastic fluid flow. At low liquid flow rates, there is an inadequacy of surrounding liquid to stabilize the bubble (FIG. 3D). Bubbles burst at the exit of the outer orifice. At times, all the large bubbles can break during the process and only the small bubbles can survive inside the smaller liquid droplets (FIG. 3E).

In some implementations, bubbles from the monodisperse state are collected. In some scenarios, bubbles that are high in gas fraction are collected. The bubbles spontaneously self-assembled into crystalline foam structures and are stable for several minutes. In some implementations, the bubbles are collected until the thickness of the liquid foam reaches a certain dimension, for example, 3 mm in thickness, in a 3-cm Petri dish. In alternative implementations, the bubbles can be collected to form different dimensions in Petri dishes of the same or different sizes. Subsequently, the alginate in the bubbles are cross-linked by exposing the alginate to a suitable crosslinking reagent to form a cross-linked solid foam. For example, a 100-mM or higher calcium chloride ($CaCl_2$) solution can be used as the crosslinking reagent and be added to cross-link the alginate. In some scenarios, the $CaCl_2$ solution can be added immediately after the bubbles are collected, and continuously for a period (e.g., a few minutes). Incomplete gelation can occur when the liquid foam is overly thick due to the limit of the ion diffusion process. Note that, in alternative implementations, other polymers can be used to encapsulate the gas. In such implementations, different techniques can be used to cross-link the polymer to form a solid foam from the liquid foam.

Figure 4A:
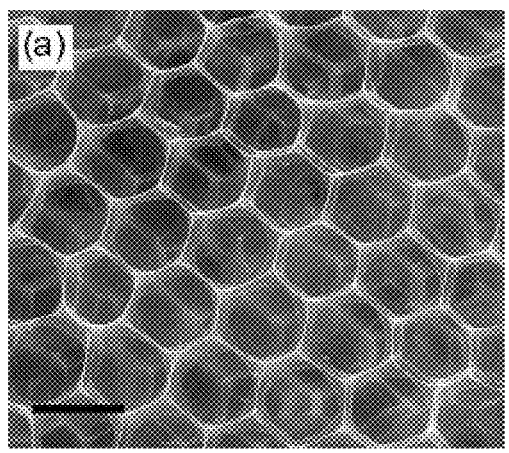
FIGS. 4A and 4B show images of an example scaffold.
Figure 4B:
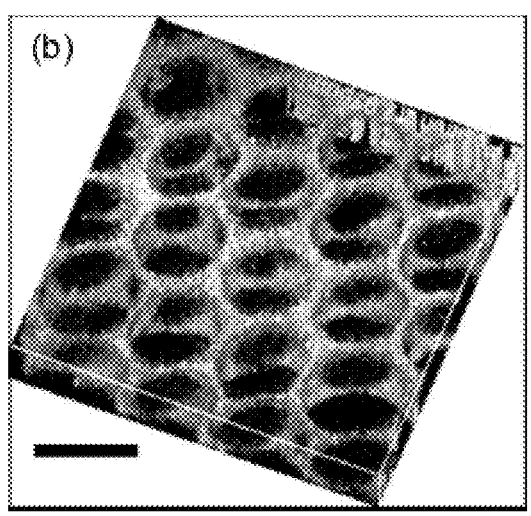

FIGS. 4A and 4B show images of Images of example scaffolds formed using the above-described techniques. When the alginate has cross-linked, the liquid foam becomes a solid foam. This solid foam is further treated or processed to form the scaffold. For example, the solid foam can be placed in liquid and degassed under vacuum until the pores are filled with water. In some scenarios, the pressure difference between the bubbles and the ambient atmosphere can rupture the film between the bubbles and only plateau borders can be left. A sliced cross-linked open-cell foam scaffold is shown in two images in FIGS. 4A and 4B. The scaffold was observed under an environmental scanning electron microscope (SEM). Fluorescent microspheres can be incorporated into the alginate solution for observation by a confocal microscope. Both, the SEM image (FIG. 4A) and the confocal image (FIG. 4B) of the scaffold, show highly ordered and interconnected pores of scaffolds. The ordered honeycomb structure was more pronounced near the surfaces of the scaffold. Deep inside the scaffold, the pore size distribution became broader than at the surfaces, but was still relatively narrow compared to traditional alginate sponge. The spatial distribution of the pores was also less ordered. Flowing of the calcium solution into alginate foam and the nonuniform gelation affected crystalline structures and the monodispersity of liquid foams. Nevertheless, the pores of scaffolds made by the above-described techniques were more controlled than the conventional sponge. The cells were cultured in the scaffolds. A process for preparing cells for injecting into the fabricated scaffolds is described with reference to FIG. 5.

Figure 5:
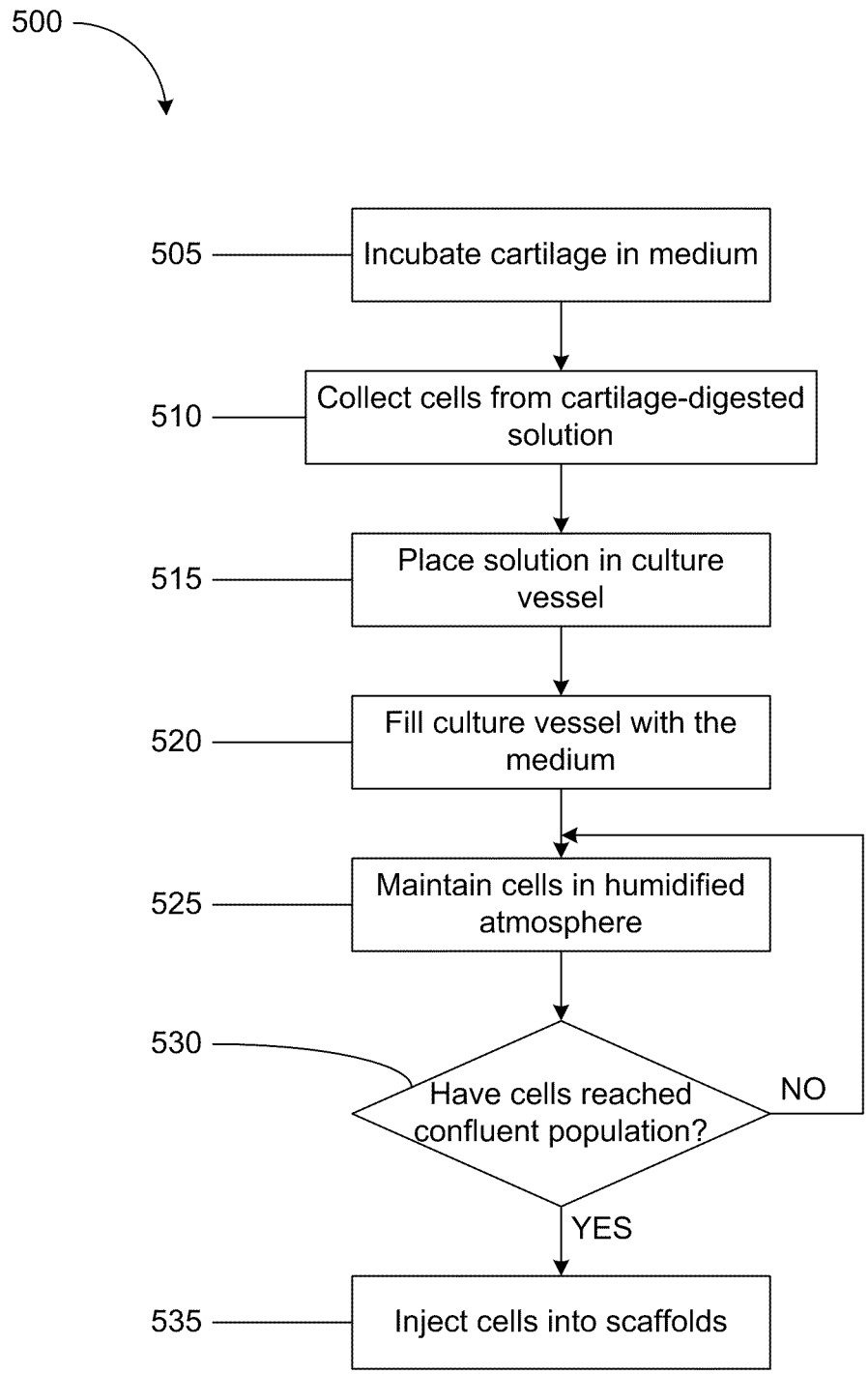
FIG. 5 is a flow chart of an example process for preparing cells for injecting into scaffolds.

FIG. 5 is a flow chart of an example process 500 for preparing cells for injecting into a scaffold. In some implementations, the process 500 can incubate cartilage in medium (505). For example, articular cartilage sliced from porcine joints can be incubated in Dulbecco's modified Eagle's medium (DMEM) containing 0.2% collegenase type II provided by Sigma Aldrich (Missouri, USA) at 37° C. for 16 hours. The process 500 can collect cells from cartilage-digested solution (510). For example, chondrocytes, the matrix-forming cells of cartilage, can be collected from a cartilage-digested solution. The process 500 can place the solution in a culture vessel (515). For example, the chondrocytes can be placed in a culture vessel. The process 500 can fill the culture vessel with the medium (520). For example, the culture vessel in which the chondrocytes are placed can be filled with the medium. The process 500 can maintain the cells in humidified atmosphere (525). For example, using a centrifuge rotated at 1500 rpm for 5 minutes, the cells can be collected and suspended in DMEM supplemented with 10% fetal bovine serum provided by Gibco (California, USA) and 50 μg/ml vitamin C provided by Sigma Aldrich (Missouri, USA). The cells can be maintained in a humidified atmosphere of 5% $CO_2$ and 95% air at 37° C.

The process 500 can test if the cells have reached confluent population (530). The confluent population can be a population that includes more than $10^6$ cells on 100 mm culture dishes. In alternative implementations, the confluent population can be greater than or less than $10^6$ cells. If the cells have not reached the confluent population, then the process 500 can continue to maintain the cells in humidified atmosphere. If the cells have reached the confluent population, then the process 500 can inject the cells into scaffolds (535). In some implementations, the scaffolds can be rinsed, for example, twice, with the culture medium in culture plates, for example, 12-well culture plates. Subsequently, the cells can be injected into the alginate scaffolds. The culture medium can then be added to the scaffold-containing well. Also, additives, for example, penicillin (100 units/ml) and streptomycin (100 μg/ml) can be added to prevent bacteria growth. In some scenarios, the plates can be transferred to an incubator at 37° C. with 5% $CO_2$, and their media can be changed once every 2 days. Images of cells cultured using the scaffolds are shown in FIGS. 6A-6C.

Figure 6A:
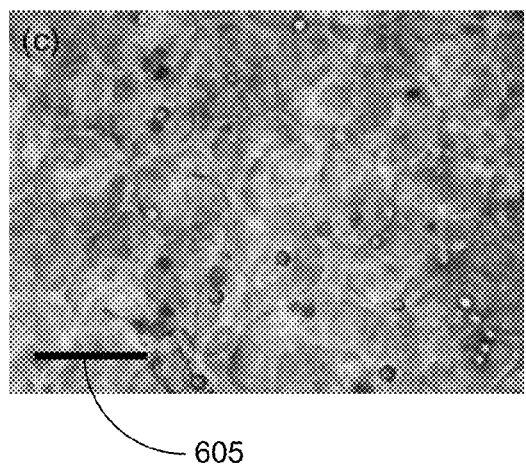
FIGS. 6A-6C show images of cells cultured in scaffolds.
Figure 6B:
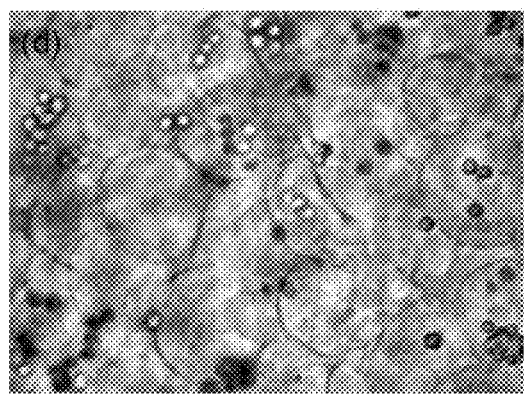
Figure 6C:
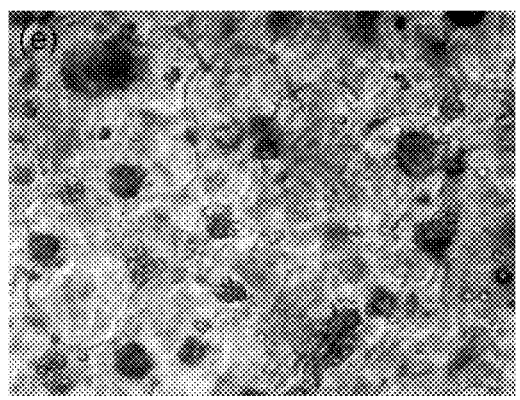

FIGS. 6A-6C show images of cells cultured in scaffolds. Specifically, the images show chondrocytes cultured in a scaffold on day 1 (FIG. 6A), day 3 (FIG. 6B), and day 7 (FIG. 6C). The dark regions in FIG. 6C are clusters of cells. The scale bar 605 shown in FIG. 6C is common to all of FIGS. 6A-6C and represents 100 μm. The process by which the scaffolds are made is summarized with reference to FIG. 7.

Figure 7:
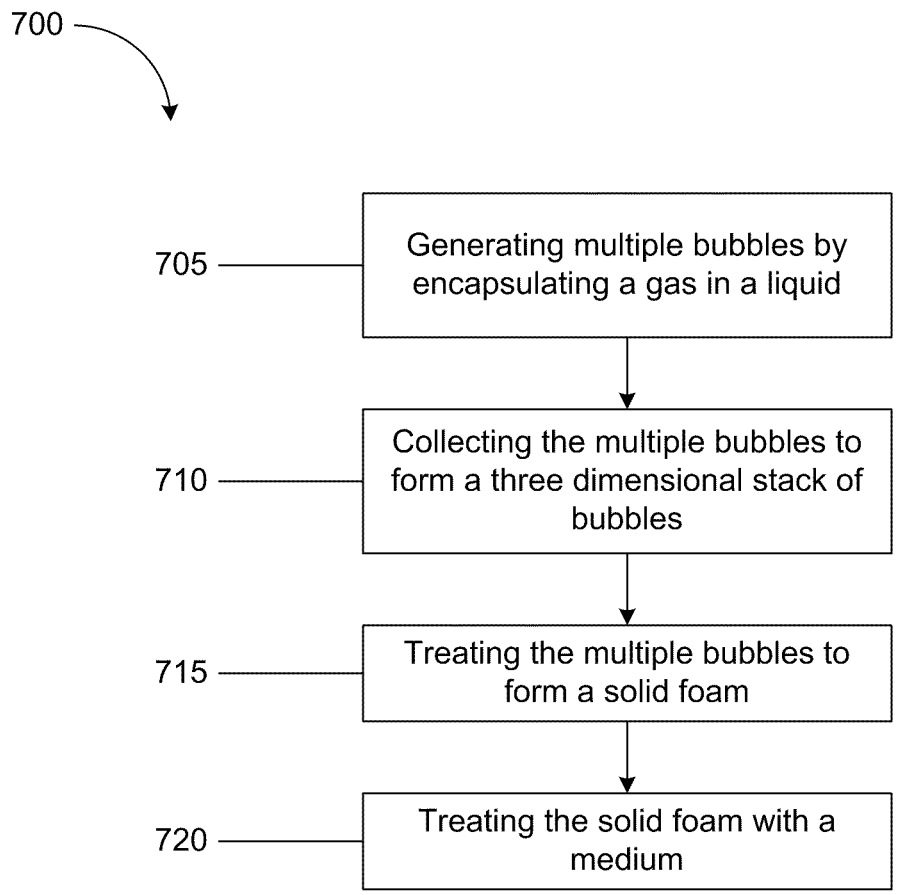
FIG. 7 is a flow chart of an example process for preparing a scaffold to culture cells.

FIG. 7 is a flow chart of an example process for preparing a scaffold to culture cells. The process 700 generates multiple bubbles by encapsulating a gas in a liquid (705). The multiple bubbles have respective diameters in a micrometer range. The liquid includes a surfactant in solution. The process 700 collects the multiple bubbles to form a 3D stack of bubbles (710). The multiple bubbles self-assemble to form a liquid foam. The process 700 treats the multiple bubbles to form a solid foam (715). The process 700 treats and processes the solid foam (720). Pursuant to the treating, the solid foam becomes a scaffold in which cells grow. In some implementations, the scaffolds in which cells are cultured are formed by generating patterns of monodisperse bubbles, each of which includes a gas encapsulated in a liquid. Techniques to generate other patterns of bubbles are described with reference to FIGS. 8A-8G.

Figure 8A:
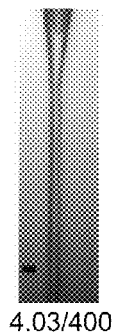
FIGS. 8A-8G show patterns of bubbles at different gas pressures/liquid flow rate.
Figure 8B:
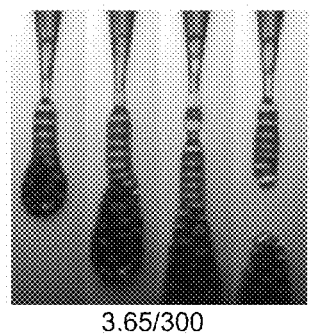
Figure 8C:
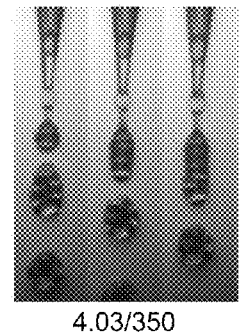
Figure 8D:
Figure 8E:
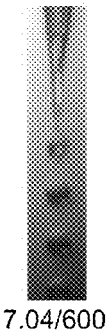
Figure 8F:
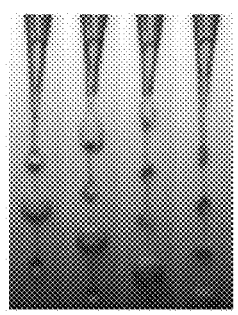
Figure 8G:
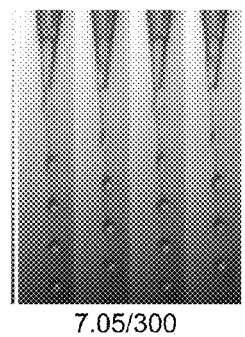

FIGS. 8A-8G show patterns of bubbles at different ratios of the gas pressure over the liquid flow rate. The size of the bubbles and the liquid droplets coming from the orifice can be controlled by controlling the gas pressure, P, and the liquid flow rate, $Q_L$. FIGS. 8A-8G show patterns of bubbles in liquid droplets at the exit of the microfluidic system 105 at different gas pressures (psi)/liquid flow rate (/min). The patterns include no bubbles, i.e., water jet (FIG. 8A), continuous bubble stream (FIGS. 8B, 8C), discontinued single bubbles (FIG. 8D), bidisperse bubbles (FIG. 8E), broken bubbles (FIG. 8F), and tiny bubbles only (FIG. 8G). FIGS. 9A, 9B, and 9C are optical images of collected bubbles corresponding to FIGS. 8D, 8E, and 8G, respectively. FIG. 10 is a state diagram of the $Q_L$ and P morphology. The solid line is used to draw the boundary where bubbles occur. The dashed line delineates the boundary where bubbles become unstable in droplets and break. The symbols describe monodisperse bubbles (solid/open circle), bidisperse bubbles (open/solid triangles), no bubbles (cross), and polydisperse bubbles (star). The open symbol denotes the occurrence of burst bubbles. All the scale bars shown are 100 μm.

Figure 11A:
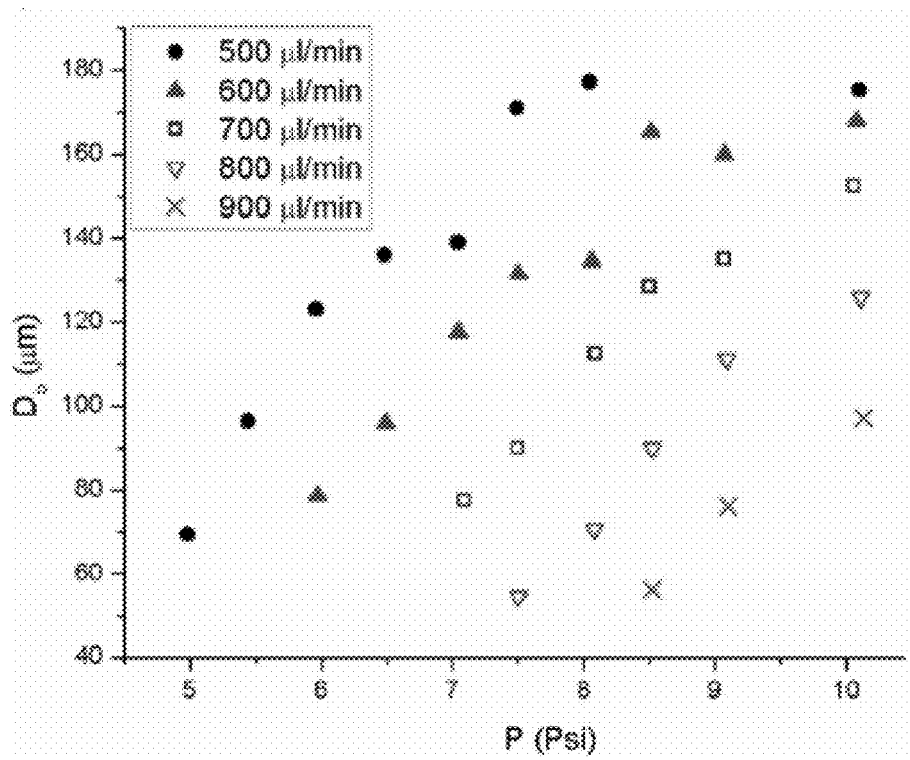
FIGS. 11A and 11B show plots of bubble diameter versus gas pressure.
Figure 11B:
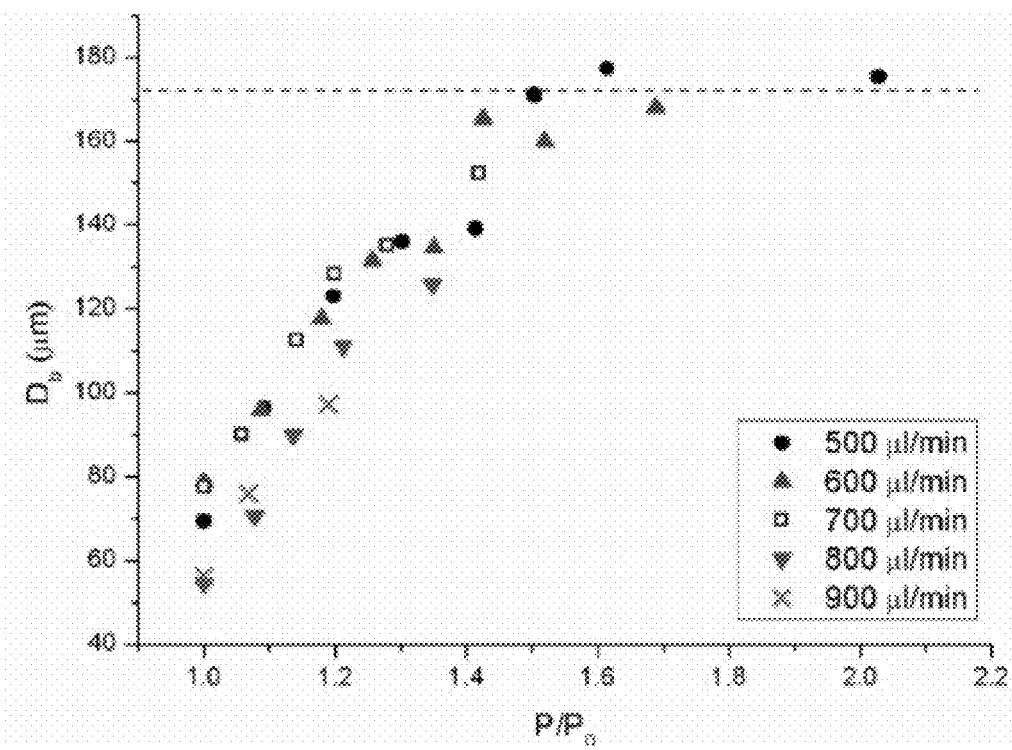

FIGS. 11A and 11B show plots of bubble diameter versus gas pressure. The diameters of the bubbles were measured from the monodisperse states and from the large bubbles from the bidisperse and the burst state. The bubble diameter, $D_b$, increased linearly with gas pressure, P, and plateaued at very high P. Diameter, $D_b$, was inversely proportional to $Q_L$ below the plateau. When P was normalized by the onset pressure $P_0$, the diameter of the bubble depended only on the ratio of $P/P_0$ and $P_0$ is proportional to $Q_L$. The plateau of the bubble diameters (indicated by the dashed line in FIG. 11B) was due to the constrained cavity created in a microfluidic system 105 having dimensions b=62 μm, h=413 μm, and B=130 μm. The equivalent spherical diameter with the same cavity volume was 181 μm. The experimental data indicated that the cavity volume at the plateau was 172 μm.

The above examples use alginate as an example for a crosslinkable material. Various other cross linkable materials can be used in connection with the techniques, structures and apparatus described in this document. Examples of suitable cross linkable materials include, but are not limited to, gelatin, collagen, polyacrylamide, cellulose, fibrin, polycaprolactone, polylactic acid, and poly lactic-co-glycolic acid. Suitable crosslinking reagents for these materials are used to contact the generated bubbles to cause the desired cross linking for producing foams of different degrees of softness or hardness.

In generation of bubbles, the sizes of the generated bubbles can controlled to be substantially uniform via controlling the mixing of the gas and the liquid. In this regard, in addition to controlling the microfluidic mixing conditions of the gas and the liquid, the content of the gas can also be controlled to improve the uniformity of the sizes of generated bubbles. In the examples described above, nitrogen is an example of a gas that is mixed with the liquid in generating bubbles. Other gases different from nitrogen can also be used. A suitable gas for this process should be biologically inert and chemically stable. In addition, a gas mixture of two or more gases can be used. In some implementations, for example, in addition to a main gas such as nitrogen, a second gas that is insoluble in water or has a low water solubility can be added to the nitrogen to improve uniformity of the bubble sizes by slowing down or extending the duration of the coarsening process. One example of such an added second gas is Perfluorohexane ($C_6F_{14}$).

Subsequent to the initial generation of the bubbles, the generated bubbles undergo conditions in subsequent processing which may cause variation of the bubble sizes. For example, after the bubbles are generated, the Laplace pressure, i.e., the pressure difference between the encapsulated gas inside the bubbles and the ambient atmosphere outside the bubbles, can vary and thus causes bubble sizes to change. Various techniques can be used after the generation of the bubbles to improve the size uniformity. For example, in forming a 2D or 3D porous matrix by collecting the generated bubbles and crosslinking the liquid in the bubbles, the crosslinked matrix can be degassed to improve the size uniformity of the final porous. As another example, the surrounding pressure at a location where the bubbles are collected can be controlled to improve the size uniformity of the collected bubbles.

FIGS. 12A and 12B show an example of an apparatus for collecting the generated bubbles from a microfluidic device. FIG. 12A shows a perspective view of the apparatus and FIG. 12B shows a cross sectional view along the line AA in FIG. 12A. This apparatus includes a substrate 1210 on which one or more bubble collecting on-chip reservoirs 1220 are formed. Each reservoir 1220 is a cavity or well formed on the surface of the substrate 1210 and can be in a desired shape, e.g., a circular, oval, rectangular or square well. An on-chip gas supply channel 1230 is formed on the substrate 1210 and is connected a respective reservoir 1220. A tube 1240 is provided to receive a flow of bubbles generated by a microfluidic device to the channel 1230 and to pass through the reservoir 1220. A portion of the bubbles in the received flow is collected inside the reservoir 1220 and the uncollected bubbles are directed out of the reservoir via the channel 1230. A removable cover 1250, such as a glass slide, is used to close the top opening of the reservoir 1220 to provide an enclosure that is separated from the ambient surrounding so that the pressure inside the reservoir 1220 during collection of the bubbles is stabilized. Therefore, the reservoir 1220 covered by the removable cover 1250 is a pressure stable environment for collecting the bubbles and improve the size uniformity of the collected bubbles.

In operation, the removable cover 1250 is first close up the top opening of the reservoir 1220 and the flow of bubbles is directed via the tube 1240 to the channel 1230 and the reservoir 1220. After the collected bubbles inside the reservoir are stabilized, the removable cover 1250 is removed and a liquid solution with a suitable crosslinking reagent is applied to the reservoir 1220 to cause crosslinking of the crosslinkable liquid of the bubbles. The foam formed by the crosslinking takes the shape of the reservoir 1220 and can be removed from the reservoir for subsequent cell growth.

In the above 2D and 3D matrices with pores formed in crosslinked materials, the cell growth is achieved by introducing cell samples into pores inside the 2D or 3D matrices. Alternatively, cell samples or biological materials may be mixed with the crosslinkable liquid in generating the bubbles so that the crosslinked porous 2D and 3D matrices are fabricated with cell samples embedded in the crosslinked material. The subsequent cell growth can be achieved by immersing the crosslinked porous 2D and 3D matrices embedded with cell samples in a suitable cell culture solution.

Figure 13:
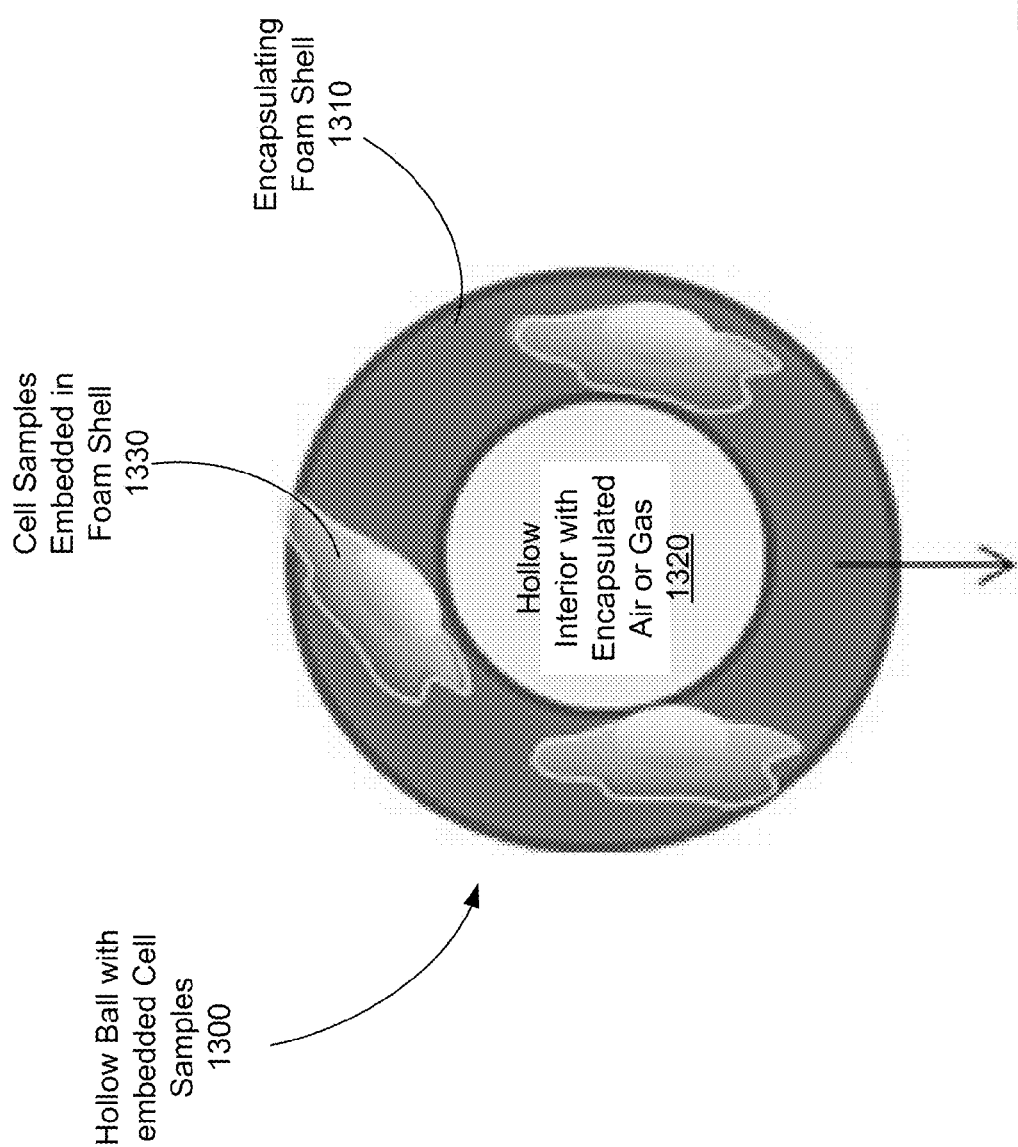
FIGS. 13 and 14 show an example of monodispersed balls with embedded cell samples in a crosslinked material and fabrication thereof.

In other applications, the above embedding cell samples in a crosslinked material can be achieved in monodispersed hollow balls without forming the above described 2D and 3D matrices. FIG. 13 illustrates an example of such a hollow ball 1300 generated based on the bubble generation based the microfluidic process described in this document. The hollow ball 1300 has an exterior foam shell 1310 with a hollow interior 1320 encapsulated by the exterior foam shell 1310. The exterior foam shell 1310 is made of a crosslinked material and is embedded with cell samples 1330. Inside the hollow interior 1320, the air or a suitable gas is enclosed and encapsulated by the exterior form shell 1310.

Figure 14:
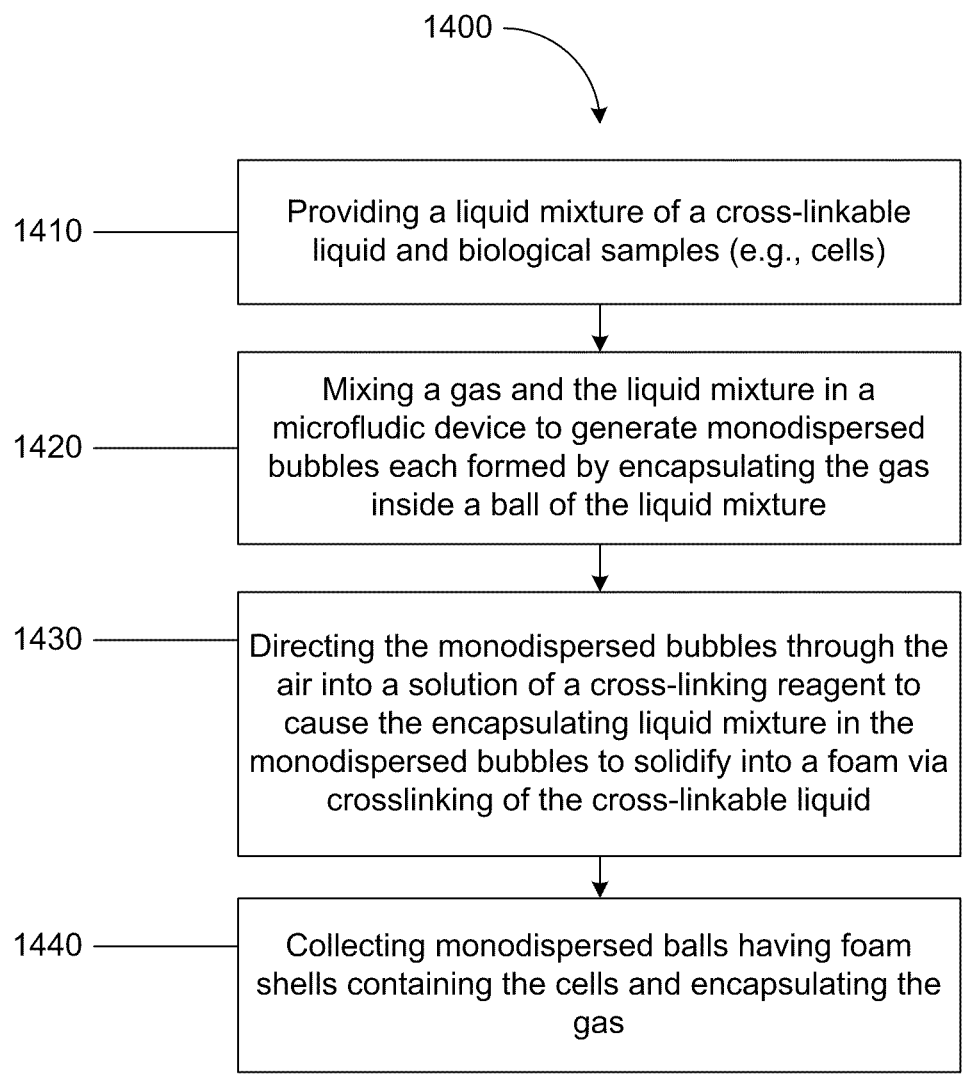

FIG. 14 shows an example of a fabrication process using the present microfluidic process to fabricate the hollow ball 1300 in FIG. 13. A liquid mixture of a cross-linkable liquid and biological samples (e.g., cells) is provided (1410) and is mixed with a gas or a gas mixture in a microfluidic device to generate monodispersed bubbles each formed by encapsulating the gas inside a ball of the liquid mixture (1420). The monodispersed bubbles are directed through the air into a solution of a cross-linking reagent to cause the encapsulating liquid mixture in the monodispersed bubbles to solidify into a foam via crosslinking of the cross-linkable liquid (1430). The above monodispersed balls having foam shells containing the cells and encapsulating the gas are collected. For cell growth, individual hollow balls or a collection of hollow balls can be placed in a suitable cell culture solution to grow cells.

While this document contains many specifics, these should not be construed as limitations on the scope of the specification or of what may be claimed, but rather as descriptions of features specific to particular implementations of the document. Certain features that are described in this document in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

In some implementations, the uniformity in pore size can be improved by increasing the stability of foam and by more controlled gelation process. The above-described techniques can be used with other scaffold materials. Complex patterns can be produced using the rigid axisymmetric coflow device described above. The structures of the droplets containing bubbles can be further engineered into new materials by polymerizing the liquid in the air. By studying the mechanism of breakup and the governing law on patterns, novel biological applications of microfluidic technology can be identified. In addition, the techniques can be used in the current research trends of biphasic flows and dynamic patterning using the microfluidic system.

Only a few implementations are described and illustrated. Variations, enhancements and improvements of the described implementations and other implementations can be made based on what is described and illustrated in this document.

What is claimed is:

1. A method for fabricating scaffolds to culture cells, comprising:
   mixing a gas with a liquid including a crosslinkable material in solution to generate gas bubbles encapsulated by the liquid having respective diameters in a micrometer range by using an inner micropipette to guide the gas and an outer micropipette that encloses the inner micropipette to form a space between the outer and inner micropipettes to guide the liquid to mix with the gas to cause the gas bubbles encapsulated by the liquid to be formed as a single stream of gas bubbles, one gas bubble at a time, to render the gas bubbles uniform in size;
   collecting the generated gas bubbles in a volume to assemble the collected gas bubbles relative to one another in form of a foam comprising the bubbles encapsulated by the liquid; and
   causing the crosslinkable material to cross-link to transform the gas bubbles into a matrix of cavities inside the foam which functions as a scaffold providing cavities for cell growth.

2. The method of claim 1, wherein the gas is nitrogen.

3. The method of claim 1, the liquid is an aqueous solution including 1% alginate and 1% surfactant.

4. The method of claim 1, further comprising regulating a gas pressure and a liquid flow rate so that diameters of the plurality of bubbles are in a range between and including 40 µm and 180 µm.

5. The method of claim 1, comprising controlling the gas pressure and the liquid flow rate to render diameters of the gas bubbles to be substantially equal to one another.

6. The method of claim 1, further comprising adding a solution containing a crosslinking reagent to the foam.

7. The method of claim 6, wherein the solution is a Calcium Chloride solution.

8. The method of claim 1, wherein treating the foam to form the scaffold comprises degassing the foam under vacuum.

9. The method of claim 1, wherein the gas includes a first gas which is biologically inert and chemically stable and a second different gas which is insoluble in water or has a low solubility in water.

10. The method of claim 9, wherein the second gas is Perfluorohexane.

11. The method of claim 1, wherein:
   the collecting of the generated gas bubbles comprises directing the generated gas bubbles via a gas supply channel into a well on a substrate that is covered by a removable cover, and
   the method comprising opening the well by removing the removable cover after the collecting and, subsequently to the opening, introducing a crosslinking reagent solution into the well to cause crosslinking of the crosslinkable material.

12. The method of claim 1, wherein the cross linkable material includes at least one of alginate, gelatin, collagen, polyacrylamide, cellulose, fibrin, polycaprolactone, polylactic acid, and poly lactic-co-glycolic acid.

13. The method of claim 1, wherein the inner micropipette has an inner outlet of a dimension in a range between and including 25 µm and 35 µm to output the gas, and the outer micropipette has an outer outlet of a dimension in a range between and including 60 µm and 75 µm.

14. The method of claim 1, wherein the outer micropipette includes an outer outlet and the inner micropipette includes an inner outlet, and
   the method further comprises setting a spacing between a surface of the inner outlet and a surface of the outer outlet to be between and including 350 µm and 450 µm.

15. The method of claim 1, wherein the inner micropipette has a frusto-conical shape, and the outer micropipette has a frusto-conical shape.

16. The method of claim 1, wherein the inner micropipette has an inner outlet with a circular cross-section.

17. The method of claim 1, wherein the outer micropipette has an outer outlet with a square cross-section.

18. The method of claim 1, wherein the gas is nitrogen.

19. The method of claim 1, wherein the liquid is an aqueous solution including a salt and a surfactant.

20. The method of claim 1, comprising adding a second different gas into the gas to mix with the liquid, wherein the second gas is insoluble in water or has a low solubility in water.

* * * * *